(12) United States Patent
Tsitlik et al.

(10) Patent No.: US 9,724,258 B2
(45) Date of Patent: Aug. 8, 2017

(54) USER CONTROL SYSTEM AND METHOD FOR INFANT CARE APPARATUS

(71) Applicant: General Electric Company, Schenectady, NY (US)

(72) Inventors: Arkadiy Tsitlik, Reisterstown, MD (US); Steven Falk, Baltimore, MD (US)

(73) Assignee: General Electric Company, Schenectady, NY (US)

( * ) Notice: Subject to any disclaimer, the term of this patent is extended or adjusted under 35 U.S.C. 154(b) by 328 days.

(21) Appl. No.: 14/230,811

(22) Filed: Mar. 31, 2014

(65) Prior Publication Data

US 2015/0272802 A1    Oct. 1, 2015

(51) Int. Cl.
*A61G 11/00*    (2006.01)
*A61B 5/145*    (2006.01)
*A61B 5/01*    (2006.01)
*A61B 5/00*    (2006.01)
*A61B 5/103*    (2006.01)

(52) U.S. Cl.
CPC ............... *A61G 11/00* (2013.01); *A61B 5/01* (2013.01); *A61B 5/14542* (2013.01); *A61B 5/746* (2013.01); *A61G 11/002* (2013.01); *A61G 11/009* (2013.01); *A61B 5/1036* (2013.01); *A61B 5/7221* (2013.01)

(58) Field of Classification Search
None
See application file for complete search history.

(56) References Cited

U.S. PATENT DOCUMENTS

| | | | |
|---|---|---|---|
| 5,750,937 A | | 5/1998 | Johnson et al. |
| 6,067,019 A | * | 5/2000 | Scott ................. A61B 5/11 340/562 |
| 6,280,392 B1 | * | 8/2001 | Yoshimi ............... A61B 5/1116 600/529 |
| 6,733,473 B1 | | 5/2004 | Reifart et al. |
| 7,656,299 B2 | * | 2/2010 | Gentry ................. A61B 5/1113 340/562 |
| 7,868,743 B1 | * | 1/2011 | Brown .................. G01G 19/56 177/12 |
| 2003/0191358 A1 | * | 10/2003 | MacKin ................ G08B 21/02 600/22 |
| 2009/0149927 A1 | * | 6/2009 | Kneuer .................... A61B 5/01 607/96 |
| 2013/0032149 A1 | * | 2/2013 | Robinson ................ A61B 5/08 128/204.21 |
| 2013/0066143 A1 | * | 3/2013 | Ten Eyck ............... A61G 11/00 600/22 |
| 2014/0179984 A1 | | 6/2014 | Cipriano |

* cited by examiner

*Primary Examiner* — Gary Jackson
*Assistant Examiner* — Qingjun Kong
(74) *Attorney, Agent, or Firm* — Andrus Intellectual Property Law, LLP

(57) ABSTRACT

An infant care system comprises a platform configured to support an infant and to receive an applied force on the platform. The infant care system also comprises at least two load cells connected to the platform, each of the two load cells configured to receive at least a portion of the applied force on the platform and generate a signal indicative of the portion of applied force received. The infant care system also comprises a processor configured to receive and analyze the signals from the load cells and perform a function based on the analyzed signals.

22 Claims, 3 Drawing Sheets

USER CONTROL SYSTEM AND METHOD FOR INFANT CARE APPARATUS

BACKGROUND OF THE INVENTION

The subject matter disclosed herein relates to an infant care apparatus. In particular, the present invention relates to a system and method of controlling the infant care apparatus.

When working inside the incubator infant compartment, it is often challenging for the caregiver to react to the incubator controller prompts or alarms. To do so, the caregiver's hands must leave the infant compartment space to either interact with the controller directly or, in some cases, use a hands free alarm silence mechanism. Depending on the nature of the caregiver's interaction with the patient inside the compartment, this may interfere with sterility requirements, slow the caregiver from acting as quickly as desired, or interrupt a procedure.

Currently all alarms, independent of their nature, cause or origin, are silenced by the same caregiver action: engaging the same "alarm silence" button. The current systems do not provide a confirmation that the caregiver understands the alarm nature, cause or origin before the caregiver silences it.

Therefore, a system comprising a user interface within the infant compartment is desired. It would allow the caregiver to react to incubator controller prompts and to silence incubator or patient alarms without removing his or her hands from the infant compartment and thereby quickly controlling the incubator while preserving sterility. Additionally, such a system could provide a method for confirming the caregiver understands the nature of the alarm, thereby potentially increasing the quality of care given to the infant.

The above-mentioned shortcomings, disadvantages and problems are addressed herein which will be understood by reading and understanding the following specification.

BRIEF DESCRIPTION OF THE INVENTION

In an embodiment an infant care system comprises a platform configured to support an infant and to receive an applied force on the platform; at least two load cells connected to the platform, each of the two load cells configured to receive at least a portion of the applied force on the platform and generate a signal indicative of the portion of applied force received; and a processor configured to receive and analyze the signals from the load cells, and perform a function based on the analyzed signals.

In another embodiment, a user interface for an infant care apparatus comprises an infant support platform comprising a plurality of zones, the platform configured to receive an applied force; a plurality of load cells connected to the platform, the load cells configured to each receive a portion of the applied force and generate a signal indicative of the portion of applied force received; and a processor configured to receive the signals from the plurality of load cells, determine in which of the plurality of zones the force was applied, and perform a function based on the zone.

In another embodiment, a method of controlling an infant care system comprises providing a platform for supporting an infant, the platform connected to a plurality of load cells; applying a force to the platform, wherein each of the plurality of load cells receives a portion of the force and generates a signal indicative thereof; determining with a processor a location of the force with respect to the platform based on the signals from the plurality of load cells; and performing with a processor a function based on the location of the force.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
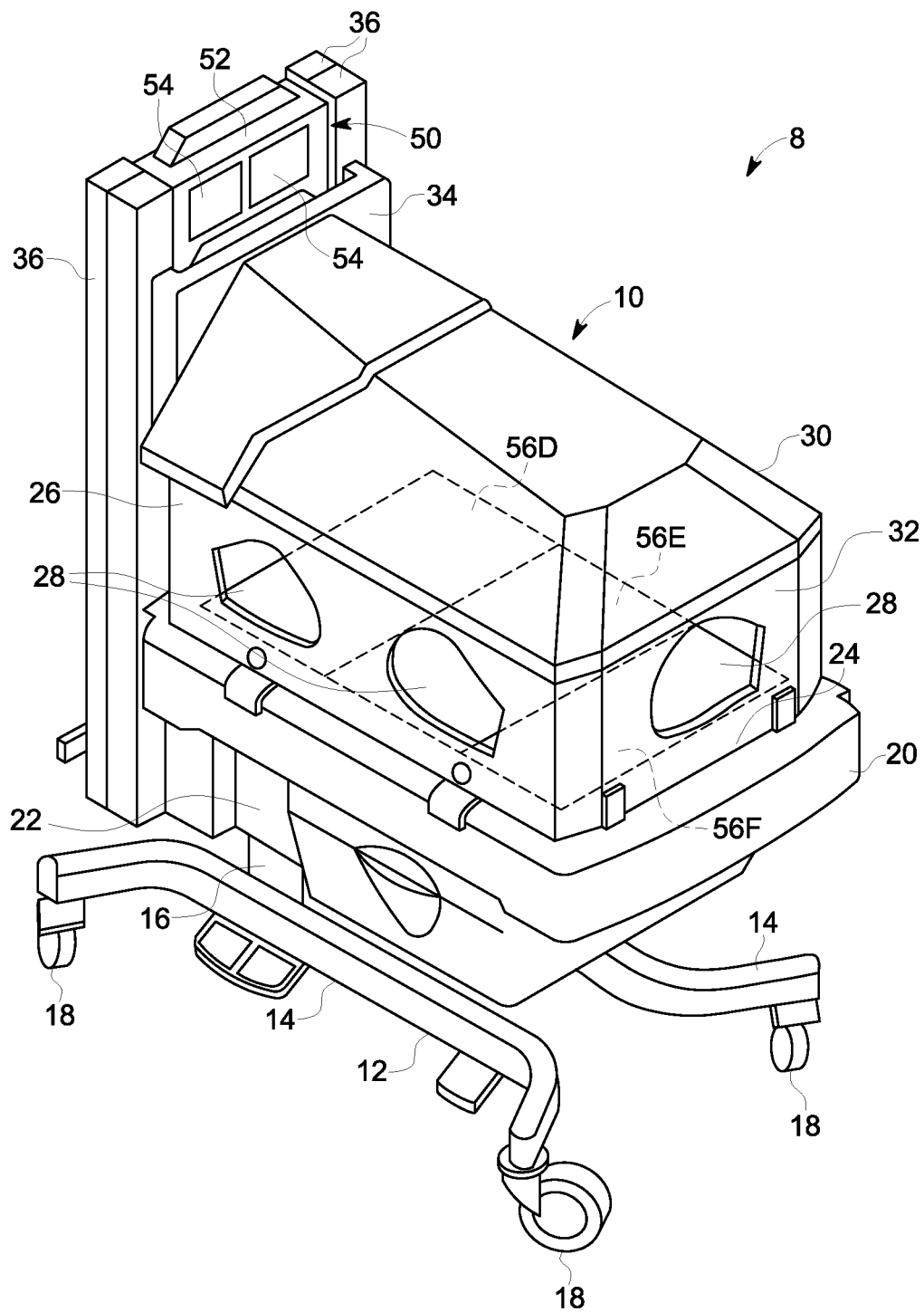
FIG. 1 is a perspective view of an infant care apparatus in accordance with an embodiment of the disclosure.

FIG. 1 is a perspective view of an infant care apparatus 10 in accordance with an embodiment of the disclosure. The infant care apparatus 10 depicted in FIG. 1 is a hybrid incubator/warmer; however, it should be appreciated that other types of infant care apparatus 10 are envisioned. For example, the infant care apparatus 10 may be an infant warmer or an infant incubator.

The infant care apparatus 10 includes a base 12 comprising a pair of U-shaped members 14 that are joined together and which provide support for a stationary vertical base member 16. Wheels 18 may provide for ready movement of the infant care apparatus 10.

A platform 20 is provided which supports an infant in the infant care apparatus 10. The platform 20 may be mounted in cantilever manner to a movable vertical base member 22 in a manner such that the user can adjust the height of the platform 20 by raising and lowering the movable vertical base member 22 with respect to the stationary vertical base member 16 to the preferred height by the user. The platform 20 includes a flat, planar surface 24 that actual underlies the infant when positioned with the infant care apparatus 10. The platform 20 may comprise a plurality of zones 56 D, E, F. It should be appreciated that the quantity and configuration or zones may vary in different embodiments. For example, in the depicted embodiment, there are three zones 56 D, E, F. In another embodiment, there may be a single zone.

Extending upwardly around the periphery of the platform 20 are a plurality of walls 26, normally of a transparent plastic material and which surround the flat planar surface 24 to enclose the infant on the flat, planar surface 24. The walls 26 can have handholes 28 to enable the caregiver to reach the infant, however, if even more access is required to the infant, at least one of the side walls 26 can be dropped downwardly to open fully for complete access to the infant to carry out procedures on the infant or for introducing and removing the infant from the infant care apparatus 10.

A hood 30, when in the position as shown in FIG. 1, may abut the upper peripheral edges of the walls 26 to enclose therein an infant compartment 32 that provides a controlled environment where heat and humidity can be controlled to aid in the development and wellbeing of the infant. The hood 30 may be of a conventional design, however, in the embodiment as shown, the hood 30 can be raised and lowered vertically to cover and uncover the infant compartment 32.

The hood 30 is affixed to a movable vertical frame member 34 that moves with respect to, and interfits with stationary vertical frame members 36. A lifting mechanism (not shown) is used to move the movable vertical frame members 34 and the hood 30 upwardly and downwardly with respect to the stationary vertical frame members 36.

A radiant heater (not shown) can also be included for providing heat to the infant when the hood 30 is in its uppermost position and thus the infant care apparatus 10 can be operated in the manner of an infant warmer or as an incubator in the configured position as shown in the present FIG. 1.

In the embodiment depicted in FIG. 1, a control module 50 is conveniently positioned intermediate the stationary vertical frame members 36 and is operatively connected to a processor 52. The control module 50 may include a display 54 to display various monitored parameters as well as include the various controls for operation of the functions of the infant care apparatus 10 and an infant care system 8. For example, the display 54 may display patient physiological parameters such as oxygen saturation ($SpO_2$), fraction of inspired oxygen ($FiO_2$), or temperature; physiological and system alarms; microenvironmental parameters such as temperature or humidity; caregiver queries or prompts; or other information related to the infant care apparatus, the infant care system, the infant or the care setting. It should be appreciated that the infant care apparatus 10 may comprise more than one display 54.

Figure 2:
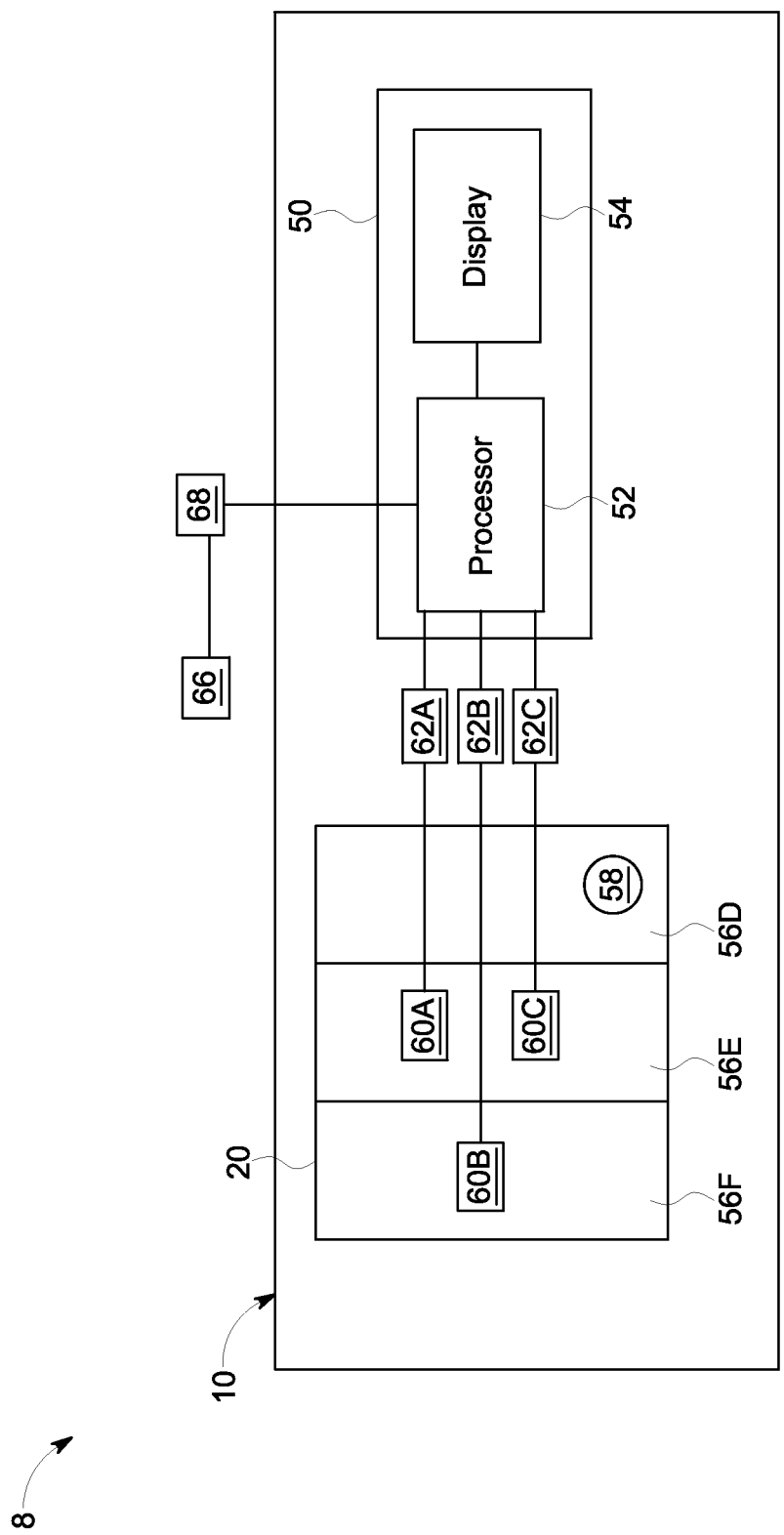
FIG. 2 is schematic diagram of an infant care system in accordance with an embodiment of the disclosure.

FIG. 2 is a schematic diagram of the infant care system 8 in accordance with an embodiment of the disclosure. Infant care system 8 comprises the infant care apparatus 10 as generally described with respect to FIG. 1, having the platform 20 that is configured to receive and support an infant. In an embodiment, the platform 20 may be a scale. The platform 20 is also configured to receive an applied force at a location 58 on the platform 20 from a user, such as a caregiver. The applied force may be a single push, a double push, or a discrete force of some other identifiable pattern. A minimum magnitude of the applied force may also be pre-defined to be equal to or above an adjustable threshold, in order to avoid unintentional applied forces. Additionally, a duration range of the applied force may also be pre-defined to avoid unintentional applied forces.

The infant care system 8 also comprises a plurality of load cells 60 connected to the platform 20. For the purpose herein, a load cell is defined as a transducer that converts a force into an electrical signal. The plurality of load cells 60 could be hydraulic load cells, pneumatic load cells, strain gauge load cells, or any other type of load cell or combination thereof. In the depicted embodiment, the infant care system 8 has three load cells 60 A, B, C and the load cells 60 A, B, C are arranged in a triangular pattern. However, it should be appreciated that other arrangements, configurations, or number of load cells may be envisioned. For example, load cells 60 A, B, C may be arranged linearly. In another example, the plurality of load cells 60 may comprise four load cells, which may be arranged in a quadrilateral formation or, alternatively, linearly. In another example, the plurality of load cells 60 may comprise two load cells, spaced apart and thereby arranged linearly.

The plurality of load cells 60 A, B, C is configured to each receive at least a portion of applied force and generate a respective signal 62 A, B, C. Signals 62 A, B, C are indicative of the portion of the applied force received by each of the load cells 60 A, B, C. The processor 52 is connected to the plurality of load cells 60 and is configured to receive the signals 62 A, B, C from the respective load cells 60 A, B, C.

The processor 52 is configured to identify the location 58 of the applied force. In the depicted embodiment, comprising three load cells 60 A, B, C, the processor 52 can identify the location 58 of the applied force by triangulation or simultaneously solving statically determinate force and moment static equilibrium equations. In another embodiment, for example comprising two load cells 60, the processor 52 can identify the location 58 of the applied force by comparing the signals 62 from the load cells.

The location 58 may be a discrete location, or the location 58 may be associated with or mapped to one or more of the plurality of zones 56. For example, in the embodiment depicted in FIG. 2, the platform 20 comprises zones 56 D, E, F, and the location of the applied force 58 is associated with zone 56 D. It should be appreciated however, that other embodiments may be envisioned with different quantities and configurations of zones. For example, the platform 20 may be divided into quadrants, each quadrant being a zone. In another example, the zones may be located around the periphery of the platform 20, so that each side of the platform 20 is a zone. In yet another example, the platform 20 may comprise a single zone that may extend over the whole flat, planar surface 24 or alternatively, over only a portion thereof.

The infant care system 8 may also comprise a sensor 66 configured to sense a patient physiological parameter and generate a physiological parameter signal 68. The sensor 66 may be an oxygen sensor to measure fraction of inspired oxygen ($FiO_2$), a temperature sensor to measure body temperature, or a pulse oximetry sensor to measure oxygen saturation ($SpO_2$). It should be appreciated, however, that other physiological sensors, such as electrocardiogram ("ECG"), or combinations thereof, may be envisioned. The processor 52 is also configured to generate alarms relating to alarm conditions of the infant care system 8 or the infant care apparatus 10. For example, an alarm may be generated when the warmer heater power is too high for a predetermined period of time. In another example, an alarm may be generated if the infant compartment 32 is below the preset temperature.

The processor 52 is configured to receive the physiological parameter signal 68 from the sensor 66. The processor 52 may be configured to process the physiological parameter signal 68 and display the data associated with the signal 68 on the display 54. The processor 52 is also configured to generate an alarm upon detection of an alarm condition. The alarm condition may be when the physiological parameter signal 68 is outside a predefined range. For example, the physiological parameter signal 68 may indicate that the temperature is too high or too low and the processor would generate an alarm related to temperature. The alarm condition may also be triggered by the occurrence an event or undesirable condition. For example, the alarm condition may also be that the sensor 66 has become disconnected or detached from the infant.

Based on the determined location 58 of the applied force, the processor 52 is also configured perform a function. The function may be alarm silence, query response or microenvironmental parameter adjustment. It should be appreciated that these embodiments of the function are non-limiting and that other embodiments of the function may also be envisioned.

In one embodiment, the function may be an alarm silence. For the purpose herein, alarm silence may be defined as the temporary or permanent inactivation of the alarm. The alarm silence may be related to an alarm generated in response to an alarm condition related to the infant physiological parameters, the infant care system 8 or the infant care apparatus 10. The alarm silence may also be function-dependent, wherein the location 58 of the applied force is associated with a particular alarm. For example, when the processor 52 generates an alarm related to $SpO_2$, a force applied generally proximate the infant's foot or in the zone closest to the infant's foot can silence the $SpO_2$-related alarm, as the $SpO_2$ sensor is attached to the infant's foot. In another example, when the processor 52 generates an alarm related to physiological temperature, a force applied generally proximate the infant's torso or in the zone closest to the infant's torso can silence the temperate-related alarm, as the physiological temperature sensor is attached to the infant's torso. In yet another example, when the processor 52 generates an alarm related to $FiO_2$, a force applied generally proximate the infant's head or in the zone closest to the infant's head can silence the $FiO_2$-related alarm as the $FiO_2$ sensor is near the infant's mouth.

In another embodiment, the function may be a query response. For example, a query may be displayed on the display 54 and the caregiver may apply a force to the platform 20 to input a response. For example, the query response may be a yes or no, wherein the yes is mapped to one of the plurality of zones, for example 56D, and the no is mapped to another of the plurality of zones, for example 56F. In another example, the query response may be "increase" or "decrease", wherein the increase is mapped to one of the plurality of zones and the decrease is mapped to another of the plurality of zones. In yet another example, the query response may be a confirmation, and the applied force at any location or in any zone on the platform 20 may be the user input.

In yet another embodiment, the function may also be a microenvironmental parameter adjustment. For the purpose herein, microenvironmental parameter adjustment may be defined as the modification of a parameter or setting relating to the infant compartment 32, the infant care apparatus 10 or the infant care system 8. For example, an applied force may be used to input an increase or decrease in microenvironmental temperature or humidity. In one embodiment, one of the plurality, such as 56D of zones may be mapped to increase microenvironmental temperature while another of the plurality of zones, such as 56F may be mapped to decrease microenvironmental temperature. In another embodiment, one of the plurality of zones may be mapped to increase in microenvironmental humidity while another of the plurality of zones may be mapped to decrease microenvironmental humidity.

It should be appreciated that the infant care system 8 may also comprise additional devices (not pictured), such as a vital signs monitor. The processor 52 may be configured to receive signals from these devices and generate alarms upon determination of alarm conditions related thereto.

Figure 3:
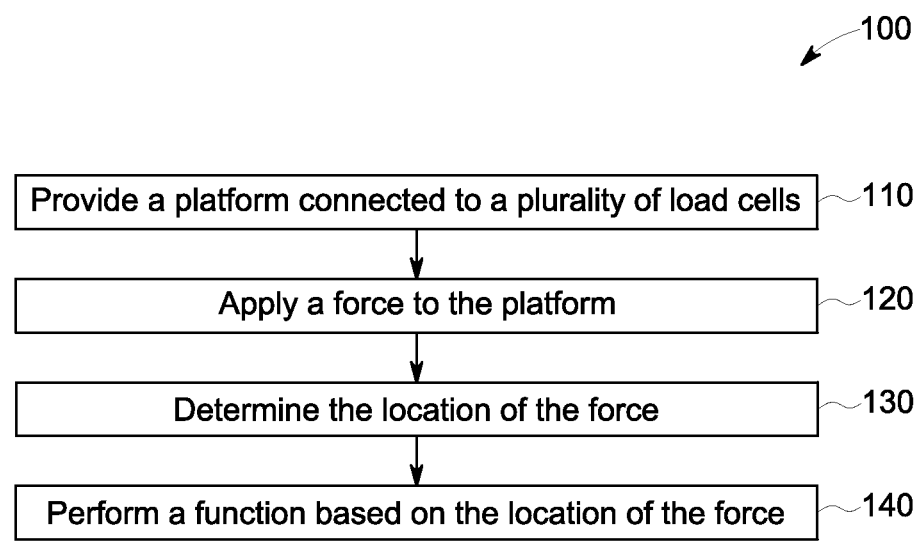
FIG. 3 is a flow diagram illustrating a method for controlling an infant care system in accordance with an embodiment of the disclosure.

Having described the components of the infant care system 8 and the infant care apparatus 10, an exemplary method 100 for controlling the infant care apparatus 10 will now be described in connection with FIG. 3. The method 100 may include a step 110 providing a platform 20 for supporting an infant, the platform 20 connected to a plurality of load cells 60. As described above with reference to FIG. 2, in the depicted embodiment, there are three load cells 60 A, B, C connected to the platform 20, and the load cells 60 A, B, C are arranged in a triangular pattern. It should be appreciated, however, that other arrangements, configurations and number of load cells 60 may be envisioned. For example, the three load cells may be arranged linearly. In another example, two load cells, spaced apart and thereby arranged linearly may be connected to the platform 20. In yet another example, four load cells may be connected to the platform 20, and the load cells may be arranged linearly or in a quadrilateral pattern.

The method 100 may include a step 120 comprising applying a force to a location 58 of the platform 20, wherein each of the plurality of load cells 60 receives a portion of the force and generates a signal 62 A, B, C indicative thereof. The applied force may be a single push, a double push, or a discrete force of some other identifiable pattern of push. A minimum magnitude of the applied force may also be pre-defined to be equal to or above an adjustable threshold, in order to avoid unintentional applied forces. A duration range of the applied force may also be pre-defined to avoid unintentional applied forces.

The method 100 may include a step 130 comprising determining with the processor 52 the location 58 of the force with respect to the platform 20 based on the signals 62 from the plurality of load cells 60. The step 130 may be made in a variety of ways. In one embodiment, the processor 52 may compare of the signals 62 from the plurality of load cells 60 and based on the signal with the highest amplitude, determine the general location 58 of the applied force. In another embodiment, the processor 52 may compare the signals 62 and identify in which of the plurality of zones 56 the force was applied. In yet another embodiment, the processor may determine a more specific location 58 of the applied force through triangulation.

The method 100 may include a step 140 comprising performing with the processor 52 a function based on the location 58 of the force. The function may be alarm silence, query response or microenvironmental parameter adjustment. In one embodiment, each of a plurality of zones 56 is mapped to a particular type of alarm. For example, when the processor 52 generates an alarm related to $SpO_2$, a force applied in the zone proximate the infant's foot, such as 56F, can silence the $SpO_2$-related alarm. In another example, when the processor generates an alarm related to physiological temperature, a force applied in the zone proximate the infant's torso, such as 56E, can silence the temperate-related alarm. In yet another example, when the processor generates an alarm related to $FiO_2$, a force applied in the zone proximate the infant's head, such as 56D, can silence the $FiO_2$-related alarm.

In another embodiment, the function may be a query response. For example, a query may be displayed on the display 54 and the caregiver may apply a force to the platform 20 to input a response. In one embodiment, the query response may be a yes or no, wherein the yes is mapped to one of the plurality of zones and the no is mapped to another of the plurality of zones. In another embodiment, the query response may be "increase" or "decrease", wherein the increase is mapped to one of the plurality of zones and the decrease is mapped to another of the plurality of zones. In yet another embodiment, the query response may be a confirmation, and the applied force at any location or in any of the plurality of zones 56 on the platform 20 may be the user input.

In yet another embodiment, the function may also be a microenvironmental parameter adjustment. For example, an applied force may be used to input an increase or decrease in microenvironmental temperature or humidity. In one embodiment, one of the plurality of zones may be mapped to increase microenvironmental temperature while another of the plurality of zones may be mapped to decrease microenvironmental temperature. In another embodiment, one of the plurality of zones may be mapped to increase in microenvironmental humidity while another of the plurality of zones may be mapped to decrease microenvironmental humidity.

The method 100 may also include setting the orientation of the infant with respect to the platform 20. This step may be accomplished by applying a force to the platform 20 at a pre-determined location. For example, a caregiver may apply a force at the end of the platform 20 nearest an infant's feet to set the location of the infant's feet with respect to the platform 20. Alternatively, a caregiver may apply a force at the end of the platform 20 nearest the infant's head to set the location of the infant's head with respect to the platform 20. It should also be appreciated that this step may be performed before or after an infant is positioned on the platform 20.

The invention described herein has many advantages. It would allow a caregiver to react to incubator controller prompts and to silence incubator or patient alarms without having to remove his or her hands from the infant compartment. This would not only help preserve sterility, but would also allow the caregiver to act quickly as it would require less movement and thereby minimize patient procedure interruption. Additionally, the implementation of the invention would not add clutter to an already crowded the infant compartment as the load cells could be contained within existing structure.

Aligning or mapping a user specific user input to an alarm conditions could ensure that caregiver does in fact understand the cause or origin of the alarm before silencing it and would decrease the chances of accidental or unintentional alarm silence. Furthermore, simultaneous alarms for multiple conditions are very common. This invention would allow different alarm silence actions for different alarms, thereby selectively silencing alarms.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. An infant care system, comprising:
    an infant support platform configured to receive an applied force on the infant support platform from a caregiver while an infant is on the infant support platform;
    at least two load cells connected to the platform, each of the two load cells configured to receive at least a portion of the applied force on the platform and generate a signal indicative of the portion of applied force received; and
    a processor configured to:
        receive the signals from each of the load cells;
        detect an alarm condition and generate an alarm;
        analyze the signals to determine that a predefined condition is met, wherein the predefined condition identifies that the applied force is from the caregiver and the predefined condition relates to one or more of a force magnitude, a force duration, a force location, and a force pattern; and
        perform a function based on the analyzed signals, wherein the function includes silencing the alarm.

2. The infant care system of claim 1, wherein the processor compares the signals from each of the two load cells and performs the function based on the comparison.

3. The infant care system of claim 1, wherein the system comprises three load cells, arranged in a triangular pattern.

4. The infant care system of claim 3, wherein the processor analyzes the signals from each of the three load cells to identify a location of the applied force from the caregiver, and determines that the signals meet the predefined condition if the location of the applied force from the caregiver is at or near the force location of the predefined condition.

5. The infant care system of claim 1, wherein the processor is configured to determine that the signals meet the predefined condition if the force pattern is a single push.

6. The infant care system of claim 1, wherein the processor is configured to determine that the signals meet the predefined condition if the force pattern is a double push.

7. The infant care system of claim 1, wherein the alarm condition relates to the infant care system or infant care apparatus.

8. The infant care system of claim 1, further comprising a sensor configured to sense a patient physiological parameter and generate a physiological parameter signal.

9. The infant care system of claim 8, wherein the patient physiological parameter is one of temperature, fractional inspired oxygen ($FiO_2$) or oxygen saturation ($SpO_2$).

10. The infant care system of claim 8, wherein the processor is further configured to receive the patient physiological parameter signal and detect the alarm condition based on the physiological parameter signal.

11. The infant care system of claim 10, wherein the patient physiological parameter is $SpO_2$, the force location of the applied force is generally proximate to a foot of the infant.

12. The infant care system of claim 10, wherein the patient physiological parameter is temperature, the force location of the applied force is generally proximate to an infant's torso.

13. The infant care system of claim 10, wherein the patient physiological parameter is $FiO_2$, the force location of the applied force is generally proximate to an infant's head.

14. The infant care system of claim 1, wherein the function includes adjusting a microenvironmental parameter.

15. The infant care system of claim 1, further comprising a display configured to display a query to the user, and wherein the function includes a response to the query.

16. A user interface for an infant care apparatus, comprising:
    an infant support platform comprising a plurality of zones, the platform configured to receive an applied force from a caregiver while the infant is on the infant support platform;

a plurality of load cells connected to the platform, the load cells configured to each receive a portion of the applied force and generate a signal indicative of the portion of applied force received; and a processor configured to:
- detect an alarm condition and generate an alarm;
- receive the signals from the plurality of load cells;
- determine that the signals meet a predefined condition, wherein the predefined condition identifies that the applied force is from the caregiver;
- determine which zone of the plurality of zones the force was applied; and
- perform a function based on the zone, wherein the function is silencing the alarm.

17. The user interface of claim 16, wherein the function further includes query response or microenvironmental parameter adjustment.

18. A method of controlling an infant care apparatus comprising:
- providing an infant support platform having a surface that supports an infant, the platform connected to a plurality of load cells configured to sense an applied force on the surface from a caregiver while an infant is on the platform;
- receiving the applied force from the caregiver to the surface while the infant is on the platform, wherein each of the plurality of load cells receives a portion of the applied force and generates a signal indicative thereof;
- determining with a processor that one or more of the signals meet a predefined condition, wherein the predefined condition identifies that the applied force is from the caregiver;
- determining with a processor a location of the applied force with respect to the surface of the platform based on the signals from the plurality of load cells; and
- performing with a processor a function based on the location of the force on the surface of the platform, wherein the function is silencing an alarm.

19. The method of claim 18, further comprising setting the orientation of the infant on the platform.

20. The method of claim 18, further comprising receiving a measurement of oxygen saturation ($SpO_2$) from a sensor on the infant, and the location of the applied force is generally proximate to a foot of the infant.

21. The method of claim 18, further comprising receiving a measurement of temperature from a sensor on the infant, and the location of the applied force is generally proximate to an infant's torso.

22. The method of claim 18, further comprising receiving a measurement of fractional inspired oxygen ($FiO_2$) from a sensor, and the location of the applied force is generally proximate to the infant's head.

* * * * *